United States Patent
Casseday et al.

(10) Patent No.: US 11,110,074 B2
(45) Date of Patent: *Sep. 7, 2021

(54) METHODS OF IMPROVING THE PHARMACOKINETICS OF DOXEPIN

(71) Applicant: Currax Pharmaceuticals LLC, Morristown, NJ (US)

(72) Inventors: Cara Baron Casseday, San Diego, CA (US); Elizabeth Ludington, San Diego, CA (US); Michael Skinner, San Diego, CA (US); Susan E. Dubé, Carlsbad, CA (US); Roberta L. Rogowski, Rancho Santa Fe, CA (US); Philip Jochelson, San Diego, CA (US); Robert Mansbach, San Diego, CA (US)

(73) Assignee: Currax Pharmaceuticals LLC, Brentwood, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/876,492

(22) Filed: May 18, 2020

(65) Prior Publication Data

US 2020/0276151 A1    Sep. 3, 2020

Related U.S. Application Data

(63) Continuation of application No. 15/436,293, filed on Feb. 17, 2017, now Pat. No. 10,653,660, which is a continuation of application No. 13/653,213, filed on Oct. 16, 2012, now Pat. No. 9,572,814, which is a continuation of application No. 13/007,334, filed on Jan. 14, 2011, now abandoned, which is a continuation of application No. 11/781,165, filed on Jul. 20, 2007, now Pat. No. 7,915,307.

(60) Provisional application No. 60/832,727, filed on Jul. 20, 2006, provisional application No. 60/833,617, filed on Jul. 24, 2006.

(51) Int. Cl.
*A61K 31/335*    (2006.01)
*A61K 31/55*    (2006.01)

(52) U.S. Cl.
CPC ............ *A61K 31/335* (2013.01); *A61K 31/55* (2013.01); *Y10S 514/923* (2013.01)

(58) Field of Classification Search
CPC ......... Y10S 14/923; A61P 25/24; A61K 31/55
See application file for complete search history.

*Primary Examiner* — Kyle A Purdy
(74) *Attorney, Agent, or Firm* — Servilla Whitney LLC

(57) ABSTRACT

Methods of improving the pharmacokinetics of doxepin in a patient.

19 Claims, 1 Drawing Sheet

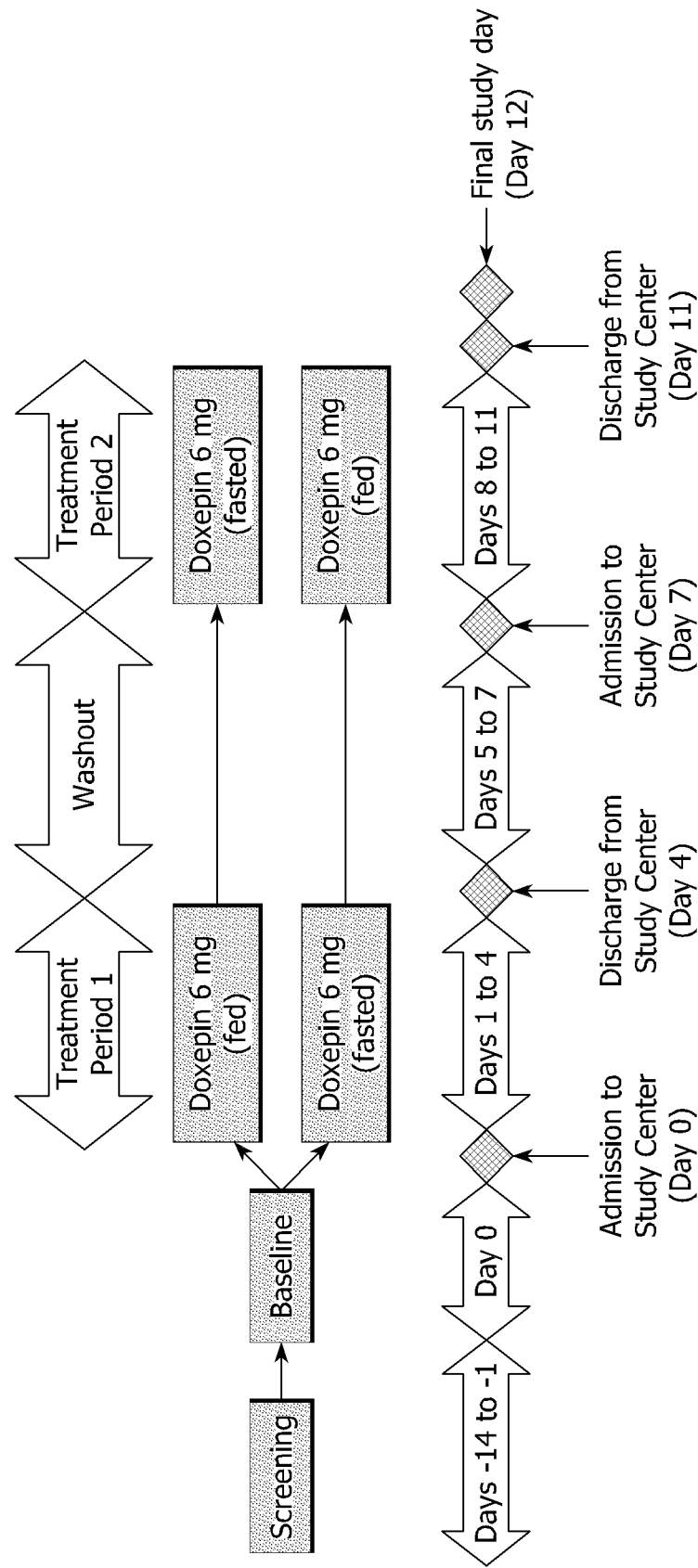

METHODS OF IMPROVING THE PHARMACOKINETICS OF DOXEPIN

CROSS-REFERENCE TO RELATED APPLICATIONS

This application is a continuation of U.S. application Ser. No. 13/007,334, filed Jan. 14, 2011, which is a continuation of U.S. application Ser. No. 11/781,165, filed Jul. 20, 2007, which claims priority to U.S. Provisional Application Nos. 60/832,727 and 60/833,617, respectively filed on Jul. 20, 2006 and Jul. 24, 2006, both entitled METHODS OF IMPROVING THE PHARMACOKINETICS OF DOXEPIN. The disclosure of each of the above-described applications is hereby incorporated by reference in its entirety.

FIELD OF THE INVENTION

The present invention relates to methods of improving the pharmacokinetics of doxepin in a patient.

BACKGROUND OF THE INVENTION

The term "food effect" refers to a somewhat unpredictable phenomenon that can influence the absorption of drugs from the gastrointestinal tract following oral administration. A food effect can be designated "negative" when absorption is decreased, or "positive" when absorption is increased and manifested as an increase in oral bioavailability (as reflected by total exposure, usually defined as AUC). Alternatively, food effects can refer to changes in maximum concentration ($C_{max}$), or the time to reach maximum concentration ($T_{max}$), independently of overall absorption. As a result, some drugs have to be taken in either fasted or fed conditions to achieve the optimum effect. For example, patients may be instructed to take a drug with a meal, before a meal (e.g., one hour before a meal), or after a meal (e.g., two hours after a meal). However, many drugs are unaffected by food, and thus, can be taken in either a fasted or a fed condition.

Doxepin is a tricyclic compound currently approved for treatment of depression and anxiety. The recommended daily oral dose for the treatment of depression or anxiety ranges from 75 milligrams to 300 milligrams. Also, U.S. Pat. Nos. 5,502,047 and 6,211,229 describe the use of doxepin for the treatment chronic and non-chronic (e.g., transient/ short term) insomnia. Doxepin, unlike most FDA-approved products for the treatment of insomnia, is not a Schedule IV controlled substance. Historically, doxepin pharmacokinetics have not been known to be affected by food.

In treating depression, anxiety and sleep disorders it is beneficial to optimize the pharmacokinetics of the administered medication in a patient. For example, in the case of sleep disorders a patient may have a set window of time within which they desire that their sleep occur. Thus, it can be useful to minimize the amount of time required to attain a maximum concentration of a drug in order to receive the therapeutic benefit of the drug as soon as possible during the desired treatment period.

SUMMARY OF THE INVENTION

Some embodiments are based upon the surprising discovery about the food effects of doxepin. For example, as described more fully below, it has been discovered that administration of doxepin without food decreases the time to achieve maximum blood concentration or $T_{max}$ for doxepin. In one experiment, the administration of doxepin without food resulted in achieving $T_{max}$ three hours more quickly than when doxepin was administered with food. As another example, it has been discovered that administration of doxepin with food increases the overall bioavailability of doxepin and results in a higher maximum concentration ($C_{max}$) of doxepin. In one experiment, the administration of doxepin with food resulted in a 41% increase in bioavailability ($AUC_{0-\infty}$) and a 15% increase in $C_{max}$ compared to administration in a fasted state.

As a result of the various discoveries related to the food effects of doxepin and depending upon the type of therapy and the desired overall result of that therapy, a patient can benefit from a number of different therapeutic regimens. Disclosed are various therapeutic regimens influenced by the food effects observed with doxepin.

Achieving a More Rapid Maximum Concentration ($T_{max}$)

In some circumstances, more rapid onset of doxepin action may be desired. One embodiment relates to a method of shortening the time required to achieve a maximum plasma concentration of doxepin in a patient receiving doxepin therapy, which method can include administering to the patient a therapeutically effective amount of doxepin in a pharmaceutical composition without food. The methods can have various benefits, including more rapid onset of drug action, shorter duration of effect, etc. The administration to the patient can occur, for example, at least about 30 minutes, at least about 1 hour, at least about 2 hours, at least about 3 hours or at least about 4 hours, or more after consuming food. Also, administration to the patient can occur at least about 30 minutes, at least about 1 hour, at least about 2 hours, at least about 3 hours, or at least about 4 hours, or more prior to consuming food, for example.

Sleep Therapy.

Another embodiment relates to methods of treating sleep disorders. A desirable sleep medication preferably can have the ability to affect the onset of drug action and the duration of drug activity (e.g., to avoid hangover, etc.). Generally, a person will desire to fall asleep as soon as possible, to stay asleep for about 8 hours, and to wake up without hangover or extra sedation at the end of the 8 hours. As mentioned above, surprisingly, the administration of doxepin without food resulted in achieving a maximum concentration of the drug three hours sooner compared to administration with food. As a result, when treating sleep, doxepin can be taken without food in order to achieve earlier onset of drug action and/or a shorter duration of drug action.

Thus, some embodiments relate to a method of shortening the time required to achieve sleep onset, which method can include administering to the patient a therapeutically effective amount of doxepin in a pharmaceutical composition without food. Also, another embodiment relates to a method of treating a sleep disorder comprising providing a patient with a therapeutically effective amount of doxepin and providing the patient with instructions to take the doxepin without food. The doxepin can be provided to the patient at least about 30 minutes, at least about 1 hour, at least about 2 hours, at least about 3 hours or at least about 4 hours or more after consuming food, or at least about 30 minutes, or at least about 1 hour prior to consuming food.

Still a further embodiment relates to a method of treating a sleep disorder comprising providing a patient with a therapeutically effective amount of doxepin and providing the patient with information regarding a doxepin food effect. The information can be provided orally or in written form. Some exemplary written forms include a label associated with the drug, on the container for the drug, packaged with the drug, or separately given to the patient apart from the drug.

Still some embodiments relate to the use of doxepin in the preparation of a medicament for treatment of a sleep disorder, said medicament for administration without food. Also, the use can further be for shortening the time required to achieve a maximal plasma concentration of doxepin by administration without food. The administration without food can occur when the patient is in a fasted state. The administration without food can occur, for example, at least about 30 minutes, at least about 1 hour, at least about 2 hours, at least about 3 hours or at least about 4 hours, or more after consuming food. Also, it can occur, for example, at least about 30 minutes, at least about 1 hour, at least about 2 hours, at least about 3 hours, or at least about 4 hours, or more prior to consuming food. In some aspects, the administration of the doxepin can occur, for example, at least about 30 minutes, at least about 1 hour, or more prior to consuming food.

Achieving a Greater $C_{max}$ or a Greater Bioavailability

Greater $C_{max}$:

Some embodiments relate to a method of increasing the maximum plasma concentration of doxepin in a patient receiving doxepin therapy comprising administering to the patient a therapeutically effective amount of doxepin in a pharmaceutical composition with food.

Greater Bioavailability:

Also, some embodiments relate to methods of increasing the oral bioavailability of doxepin, including by administering to a patient an amount of a pharmaceutical oral dosage form of doxepin with food. Further embodiments relate to methods of increasing the oral bioavailability of doxepin to a patient receiving doxepin therapy, which methods can include administering to the patient an amount of a pharmaceutical oral dosage form of doxepin with food, wherein the administration results in an $AUC_{0-\infty}$ that is greater than that achieved by the administration of the same amount of doxepin without food. In such methods, the doxepin can be administered as part of a chronic doxepin therapy, for example.

Anxiety/Depression Therapy:

Still another embodiment relates to methods of treating depression or anxiety. It is worth noting that improved pharmacokinetics of doxepin in the context of depression or anxiety can be beneficial, for example by, leading to more safe and effective dosing. The methods of treating depression or anxiety can include administering a therapeutically effective amount of doxepin preferably with food. In some embodiments the depression or anxiety can be treated by administering doxepin without food. Also, some embodiments relate to methods of treating depression or anxiety, including by providing a patient with a therapeutically effective amount of doxepin and providing the patient with instructions to preferably take the doxepin with food. In some alternative embodiments, the instructions can specify taking the doxepin without food.

Another embodiment relates to a method of treating depression or anxiety comprising providing a patient with a therapeutically effective amount of doxepin and providing the patient with information regarding a doxepin food effect.

Also, some embodiments relate to the use of doxepin in the preparation of a medicament for treatment of a psychological disorder, said medicament for administration with food. The disorder can preferably be depression or anxiety. The use also can be for the preparation of a medicament for increasing the oral bioavailability of doxepin by administration with food; for increasing the oral bioavailability of doxepin to a patient receiving doxepin therapy by administering an amount of a pharmaceutical oral dosage form of doxepin with food, wherein the administration results in an $AUC_{0-\infty}$ that is greater than that achieved by the administration of the same amount of doxepin without food; for increasing the time required to achieve a maximal plasma concentration of doxepin by administration with food; for minimizing side effects associated with a doxepin treatment of the psychological disorder, by administering a therapeutically effective amount of doxepin with food, which can result in the patient receiving or in a physician prescribing a lower dosage of doxepin compared the dosage that is taken by the patient without food; or for improving the consistency of pharmacokinetics associated with doxepin therapy, in which a patient receives a multiple doxepin dosages over multiple days, comprising administering the doxepin in a fixed temporal relationship to food intake by the patient.

Decreasing Bioavailability:

It should be noted that some embodiments relate to methods of decreasing the oral bioavailability of doxepin. Decreasing oral bioavailability can be beneficial in some contexts. For example, as mentioned above for sleep therapies, it can be beneficial to shorten the duration of the drug action in order to minimize hangover or other effects. The methods of decreasing bioavailability can include administering to a patient an amount of a pharmaceutical oral dosage form of doxepin without food. Furthermore, some embodiments relate to methods of decreasing the oral bioavailability of doxepin to a patient receiving doxepin therapy, comprising administering to the patient an amount of a pharmaceutical oral dosage form of doxepin without food, wherein the administration results in an $AUC_{0-\infty}$ that is less than that achieved by the administration of the same amount of doxepin with food. In such methods, doxepin can be administered as part of a chronic doxepin therapy, for example. Also, in such methods administration to the patient can occur, for example, at least about 30 minutes, at least about 1 hour, at least about 2 hours, at least about 3 hours or at least about 4 hours, or more after consuming food. Also, administration to the patient can occur at least about 30 minutes, at least about 1 hour, at least about 2 hours, at least about 3 hours, or at least about 4 hours, or more prior to consuming food, for example.

Minimizing Doxepin Side Effects and Improving Pharmacokinetic Consistency

Some embodiments relate to methods of minimizing side effects associated with a doxepin therapy. The methods can include, for example, administering a therapeutically effective amount of doxepin to a patient with food. Also, the administration of doxepin with food can result in a patient receiving or a physician prescribing a lower dose of doxepin compared to the dosage prescribed without food.

This disclosure includes a method for improving the consistency of pharmacokinetics associated with doxepin therapy, in which a patient receives multiple doxepin dosages over multiple days, comprising administering the doxepin to the patient in a fixed temporal relationship to food intake by the patient. This can, for example, include providing written or verbal instructions to the patient to take the doxepin in a fixed temporal relationship to food intake by the patient. Taking doxepin in a fixed relationship to food can help assure more consistent efficacy of the medication.

Other Food Effect Methods

Also, some embodiments relate to methods of alleviating a doxepin food effect or altering a doxepin pharmacokinetic parameter in a patient, for example, by administering doxepin to a patient in need thereof, wherein the patient is in a non-fasted state or in a fasted state.

Further embodiments relate to a method of treating a disorder with doxepin comprising providing a patient with a therapeutically effective amount of doxepin and providing the patient with information regarding a doxepin food effect. The information can include, for example, instructions to take the doxepin with or without food, or to ensure that doxepin is consistently taken either with or without food. The information can be in an oral or written form. Some exemplary written forms include a label associated with the drug, on the container for the drug, packaged with the drug, separately given to the patient apart from the drug, or provided in manner that the patient can independently obtain the information (e.g., a website).

Dosage and Compositions

Again, in the various disclosed embodiments, the amount of doxepin, including the therapeutically effective amount, may advantageously be, for example, about 0.001 milligram to about 350 milligrams, preferably about 50 milligrams to about 300 milligrams or more preferably about 75 milligrams to about 300 milligrams, or any amount or sub-range within those ranges. Alternatively, the effective amount may be about 0.5 milligrams to about 20 milligrams, more preferably about 1 milligram to about 6 milligrams.

Also, in the various disclosed embodiments, the pharmaceutical composition of doxepin can be, for example, a tablet, capsule or liquid. Furthermore, the doxepin can be provided or administered as a unit dosage form. Preferably, the doxepin can be provided or administered as an oral dosage form.

Doxepin Kits and Products

Finally, the present disclosure also includes a kit or a product that includes doxepin and written instructions or information associated therewith to take the doxepin without food. For example, the instructions can specify that doxepin be administered to the patient at least about 30 minutes, at least about 1 hour, at least about 2 hours, at least about 3 hours, at least about 4 hours or more after consuming food, or at least about 30 minutes, at least about 1 hour, at least about 2 hours, at least about 3 hours, at least about 4 hours or more prior to consuming food, for example. In some aspects, the kits or product can include instructions that describe administration to the patient preferably at least about 30 minutes or at least about 1 hour prior to consuming food. The kit or product can include information regarding a food effect associated with doxepin. Alternatively, it includes a kit or a product comprising doxepin and written instructions associated therewith to take the doxepin with food.

The product or kit can include doxepin in amount of about 0.5 milligram to about 350 milligrams, preferably about 50 milligrams to about 300 milligrams or more preferably about 75 milligrams to about 300 milligrams. Alternatively, the amount may be about 0.5 milligrams to about 20 milligrams, more preferably about 1 milligram to about 6 milligrams. Some preferred amounts are about 1 milligram, about 3 milligrams and about 6 milligrams.

Finally, the product or kit can include doxepin as a tablet, a capsule, a liquid, a unite dosage form or an oral dosage form, for example.

BRIEF DESCRIPTION OF THE DRAWINGS

FIG. 1 illustrates the design of a study of food effect associated with doxepin.

DETAILED DESCRIPTION OF THE INVENTION

Embodiments described herein relate to the novel and unexpected discovery of a food effect associated with doxepin. As described more fully below, a single-center, phase 1, randomized, open-label, single dose, two-way crossover study was conducted in 16 healthy young adult male and female volunteers. A food effect was observed on the pharmacokinetics of doxepin. In the fed state, pharmacokinetic parameters ($AUC_{0-\infty}$ and $C_{max}$) of doxepin were approximately 41% and 15% higher, respectively, compared to the fasted state, and median $T_{max}$ was delayed by approximately 3.0 hours in the fed state. The increase in AUC was statistically significant and demonstrates a positive food effect on exposure. The increased $T_{max}$ in the fed state suggests that food slows the absorption of the drug.

Accordingly, some embodiments relate to methods of improving the pharmacokinetics of doxepin in a patient. As discussed above and more fully elsewhere herein, administration of doxepin in a fasted state can result in decreasing the time required to achieve a maximum plasma concentration of doxepin. In particular, the time to reach maximum concentration ($T_{max}$) of doxepin can be minimized by administering the drug without food. Also, as discussed above and more fully elsewhere herein, administration of doxepin with food can increase the overall bioavailability of the drug. For example, the time to reach maximum concentration can be increased by administering doxepin with food and the bioavailability of the drug can be increased.

In addition, in a different embodiment, the total effective amount of drug that the patient receives can be maximized by administering doxepin with food, while in other embodiments the oral bioavailability of doxepin can be decreased by administering the doxepin without food. Because plasma concentrations and half-lives of doxepin are already known to vary from patient to patient, knowledge of the doxepin food effect can help patients and physicians to eliminate this additional source of dosing uncertainty, to improve safety and tolerability, and improve therapies that utilize doxepin. For example, as described more fully elsewhere herein, depending on the effect desired, doxepin can be taken with food; it can be taken after the patient has gone without food for a period of time; and/or it can be taken some period of time prior to consuming food.

As a result of the food effect discovery, various improved therapeutic methods are provided, including: where short term exposure is desired, with a more rapid onset and shorter duration of effect, doxepin preferably can be taken without food; in order to increase the bioavailability of the drug where rapid onset and shorter duration are not issues, doxepin preferably can be taken with food; and to assure more consistent efficacy, doxepin preferably can be taken in a fixed relationship to food consumption, regardless of whether the drug is taken with our without food. Short term exposure with more rapid onset can be preferable when treating, for example, a sleep disorder, while increased bioavailability and/or consistent kinetics can be preferable for treating conditions such as depression and anxiety.

Doxepin HCl is a tricyclic compound currently approved for treatment of depression and anxiety. The recommended daily dose for the treatment of depression or anxiety ranges from 75 milligrams to 300 milligrams. Also, U.S. Pat. Nos. 5,502,047 and 6,211,229, the entire contents of which are incorporated herein by reference, describe the use of doxepin for the treatment chronic and non-chronic (e.g., transient/short term) insomnias at dosages below those used to treat depression. A food effect associated with doxepin treatment of currently approved disorders or sleep disorders has not previously been reported.

Methods of Improving the Pharmacokinetics of Doxepin

Some embodiments relate to methods of improving the pharmacokinetics of doxepin, including by administering doxepin with or without food. A number of pharmacokinetic parameters can be affected by taking doxepin with or without food, including for example, $T_{max}$, $C_{max}$, and the area under the curve (AUC). Furthermore, various therapeutic regimens can be utilized to take advantage of the doxepin food effects.

Affecting Maximum Concentration ($T_{max}$):

As discussed above, administration of doxepin without food or in a fasted state can result in shortening the time required to achieve a maximum plasma concentration ($T_{max}$) of doxepin. Achieving a shorter $T_{max}$ can be desirable since onset of drug action can be more rapid and the duration of drug action may be shortened. Some embodiments relate to methods of shortening the time required to achieve a maximum plasma concentration or a $T_{max}$ of doxepin in a patient receiving doxepin therapy, which methods can include administering to the patient a therapeutically effective amount of doxepin in a pharmaceutical composition without food.

Also, it should be noted that other embodiments relate to methods of increasing the time required to achieve a maximum concentration of doxepin in a patient by administering doxepin with food.

Some embodiments relate to methods of preventing a doxepin food effect in order to minimize the time required for onset of action of the drug. The methods can include administering doxepin to a patient in need thereof, wherein the patient is in a fasted state or has not eaten or will not eat within a particular time period. The methods further can include providing instructions to take the doxepin without food or in a fasted state.

Use of Doxepin in Sleep-Related Indications:

Knowledge of the food effect disclosed herein is useful in determining an optimum regimen for providing doxepin sleep therapy. In patients receiving sleep therapy, the onset of action is an important consideration. The studies disclosed herein demonstrate that taking doxepin with food can significantly increase $T_{max}$. As a result, sleep patients who take doxepin without food would be expected to have faster sleep onset or faster drug action in comparison to those who take doxepin with food.

Thus, some embodiments relate to improved methods of treating a sleep disorder. The methods can include providing a patient with a therapeutically effective amount of doxepin and providing the patient with instructions to take the doxepin without food. In some aspects, doxepin can be administered without food in order to minimize the amount of time to achieve sleep onset or to otherwise minimize the amount of time before drug action occurs.

The information regarding the doxepin food effect can be provided to the patient. The information can include, for example, instructions that may be provided to patients receiving doxepin therapy or health care professionals involved in treatment of those patients that the doxepin should be administered without food, preferably separated from food for the time periods discussed above. By way of example, such instructions could be provided orally or in written form. Some exemplary written forms include a label associated with the drug, on the container for the drug, packaged with the drug, or separately given to the patient apart from the drug, including providing the patient with access to a website or other electronic information with the instructions/information.

Affecting Overall Concentration ($C_{max}$) or Bioavailability:

The maximum plasma concentration or overall bioavailability of doxepin can be affected by food or a lack thereof. Increasing concentration or bioavailability can be desirable in some circumstances. Some embodiments relate to methods of increasing the oral bioavailability of doxepin to a patient receiving doxepin therapy. The methods can include administering to the patient a pharmaceutical oral dosage form of doxepin with food. The administration can result in a greater AUC than if the drug is taken without food. The methods can include administering to the patient a therapeutically effective amount of doxepin in a pharmaceutical composition with food or within a relatively short time of consuming food (e.g., 15 minutes, 30 minutes, one hour, etc.).

Also, some embodiments relate to a method of increasing the maximum plasma concentration of doxepin in a patient receiving doxepin therapy comprising administering to the patient a therapeutically effective amount of doxepin in a pharmaceutical composition with food.

It should be noted that other embodiments relate to methods of decreasing the oral bioavailability or AUC of doxepin by administering doxepin without food.

Use of Doxepin in Depression and Anxiety:

Doxepin has been used for several decades in the treatment of depression and anxiety. Several side effects have been reported in connection with the use of doxepin to treat depression or anxiety. The studies disclosed herein show that by taking doxepin with food, AUC was increased by 41% compared to taking doxepin in a fasted state. Because AUC (bioavailability) is increased by taking doxepin with food, a patient can take a lower dose compared to when a patient takes doxepin without food. Increasing the oral bioavailability or AUC of doxepin, and decreasing dosage required for treatment can minimize or alleviate side effects and improve the safety and tolerability of doxepin therapy. Thus, in some aspects it can be preferred that patients receiving doxepin for depression or anxiety should take the drug with food, or in close proximity to eating. Some embodiments relate to improved methods of treating depression and anxiety. The methods can include providing a patient with a therapeutically effective amount of doxepin and providing the patient with instructions to take the doxepin with food. As discussed more fully herein, administering doxepin with food can result in an increase in the bioavailability of doxepin. As a result a patient can take less doxepin, which can be safer and more tolerable for the patient.

In some aspects, information, including instructions may be provided to patients receiving doxepin therapy or health care professionals involved in treatment of those patients regarding a doxepin food effect and/or that the doxepin should be administered with food, or at least in relatively close proximity to eating food or eating a meal (for example, within one hour or less). By way of example, such information or instructions could be provided orally or in written form. Some exemplary written forms include a label associated with the drug, on the container for the drug, packaged with the drug, or separately given to the patient apart from the drug, including providing the patient with access to a website or other electronic information with the instructions/information. The invention further includes a package of doxepin with such written instructions associated therewith.

It should be noted that some aspects of the invention also relate to methods of treating depression or anxiety by administering doxepin without food. Such embodiments can also include instructions to take the medication without food.

Improved Pharmacokinetic Consistency and Efficacy:

Still further embodiments relate to methods for improving the consistency of pharmacokinetics associated with doxepin therapy, in which a patient receives a multiple doxepin dosages over multiple days. The methods can include administering the doxepin to the patient in a fixed temporal relationship to food intake by the patient. Also, the method can further include providing instructions to the patient to take the doxepin in a fixed temporal relationship to food intake by the patient. As discussed more fully herein, taking doxepin in fixed or consistent temporal relationship to food can lead to improved safety and tolerability for the patient, for example, due to less variability in the drug kinetics in the patient.

Kits and Products:

Furthermore, some embodiments relate to kits and products for a therapy that includes the use of doxepin. The kits and products can include doxepin and instructions to take the doxepin without food or in a fasted state, or to take the doxepin with food or within a predetermined period of eating food.

The instructions or information regarding a food effect can be provided orally or verbally, or could be in written form. Some exemplary written forms include a label associated with the drug, on the container for the drug, packaged with the drug, or separately given to the patient apart from the drug, including providing the patient with access to a website or other electronic information with the instructions/information. The invention further includes a package of doxepin with such written instructions associated therewith or with information on where to access the instructions/information (e.g., a website).

Administration of Doxepin

In performing the methods, doxepin, a pharmaceutically acceptable salt of doxepin, or prodrug of doxepin can be administered in any suitable oral form. Also, doxepin, or a pharmaceutically acceptable salt or a prodrug thereof can be administered to a patient. (It should be understood that the term "administer" and its variants are intended to cover both self-administration and administration by another person or by a device.).

Doxepin can be administered without food or in a fasted state. For example, doxepin can be administered at least about 30 minutes to about 4, 5, 6 or more hours after consuming food. More preferably, doxepin can be taken at least about 1 hour to about 6 hours after consuming food. In some aspects doxepin can be taken at least about 1, 2, 3, 4, 5 6 or more hours after consuming food.

Also, doxepin can be administered at least about 30 minutes to about 6 hours before consuming any food, or more preferably, at least about 1 hour to about 3 hours before consuming food. In some aspects, doxepin can be administered about 1, 2, 3 or more hours before food is consumed.

In some embodiments of the invention, such as when doxepin is used to facilitate sleep, instructions may be provided to patients receiving doxepin therapy or health care professionals involved in treatment of those patients that the doxepin should be administered without food, preferably separated from food for the time periods discussed above. Also, the patient can be provided with information regarding a doxepin food effect. In other embodiments of the invention, such as when doxepin is used to treat depression or anxiety, instructions may be provided to patients receiving doxepin therapy or health care professionals involved in treatment of those patients that the doxepin should be administered with food, or at least in relatively close proximity to eating food or eating a meal (for example, within one hour or less).

Again, by way of example, such instructions or information regarding a food effect could be provided orally or verbally, or could be in written form. Some exemplary written forms include a label associated with the drug, on the container for the drug, packaged with the drug, or separately given to the patient apart from the drug, including providing the patient with access to a website or other electronic information with the instructions/information. The invention further includes a package of doxepin with such written instructions associated therewith.

It should be recognized that in some cases, the food effect disclosed herein can appropriately play a part in designing customized dosing regimens that reflect the preferences of a particular healthcare professional or their patient. Thus, for example, in doxepin therapy (e.g., chronic doxepin therapy), such as therapy for depression or anxiety, it is customary to titrate the dosage; in other words, typically start with a lower dose and then increase it to the minimum dose that is sufficiently effective for the patient in question. In this type of situation, there may be instances when doxepin is administered without food, even though more drug will be required to achieve the same effect. In such cases, consistency is important to maintaining equivalent pharmacological effects. In other words, if a patient on chronic doxepin therapy is receiving a titrated dose that has been determined when the patient is consistently taking doxepin with food, or consistently taking doxepin without food, then food-induced variations in doxepin pharmacokinetics should not be a factor in therapeutic response or side effects. Thus, for chronic doxepin therapy, one embodiment includes administering doxepin in a consistent relationship to food intake, regardless of whether it is or is not taken with food.

Suitable routes of administration of doxepin can include any route in which significant quantities of drug reach the stomach, including oral, buccal, and sublingual administration.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Administration though oral pathways can be accomplished, for example, using a capsule, a tablet, a granule, a spray, a syrup, a liquid, powder, granules, pastes (e.g., for application to the tongue). Oral administration can be accomplished using fast-melt formulations, for example. For example, rapidly-melting strips or sheets that include the drug and suitable excipients can be prepared that dissolve quickly in the mouth, using well-known formulation technology. For buccal or sublingual administration, the compositions may take any suitable form, for example, tablets or lozenges. Pharmaceutical preparations for oral use can be obtained by mixing one or more solid excipient with pharmaceutical combination of the invention, optionally grinding the resulting mixture, and processing the mixture of granules, after adding suitable auxiliaries, if desired, to obtain tablets or dragee cores.

Pharmaceutical preparations which can be used orally include for example, liquid solutions, powders, and suspensions in bulk or unit dosage forms. Also, the oral formulations can include, for example, pills, tablets, granules, sprays, syrups, pastes, powders, boluses, pre-measured ampules or syringes, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

A variety of techniques for formulation and administration can be found in *Remington: The Science and Practice of Pharmacy* ($20^{th}$ ed., Lippincott Williams & Wilkens Publishers (2003)), which is incorporated herein by reference in its entirety.

Compositions

As mentioned above, doxepin, pharmaceutically acceptable salts, and/or prodrugs of the same can be used alone or in combination with other substances, such as for example, other insomnia or sleep medications, or with other medications that treat a primary illness. Doxepin alone or in combination with other drugs can be included as part of a composition. The compounds and compositions can include any suitable form of the compound for pharmaceutical delivery, as discussed in further detail herein.

The compositions and formulations disclosed herein also can include one or more pharmaceutically acceptable carrier materials or excipients. Such compositions can be prepared for storage and for subsequent administration. Acceptable carriers or diluents for therapeutic use are well known in the pharmaceutical art, and are described, for example, in the incorporated material of *Remington: The Science and Practice of Pharmacy* ($20^{th}$ ed, Lippincott Williams & Wilkens Publishers (2003)), which is incorporated herein by reference in its entirety. The term "carrier" material or "excipient" herein can mean any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include sugars (such as lactose, sucrose, mannitol, sorbitol), starch powder, maize starch, wheat starch, rice starch, potato starch, gelatin, gum tragacanth, methyl cellulose, hydroxypropylmethyl-cellulose, sodium carboxymethylcellulose, or derivatives thereof, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone (PVP), and/or polyvinyl alcohol, saline, dextrose, lecithin, albumin, sodium glutamate, cysteine hydrochloride, and the like. Examples of suitable excipients for soft gelatin capsules include vegetable oils, waxes, fats, semisolid and liquid polyols. Suitable excipients for the preparation of solutions and syrups include, without limitation, water, polyols, sucrose, invert sugar and glucose. Suitable excipients for injectable solutions include, without limitation, water, alcohols, polyols, glycerol, and vegetable oils. If desired, the compositions can include disintegrating agents may be added, such as the cross-linked polyvinyl pyrrolidone, agar, or alginic acid or a salt thereof such as sodium alginate. The pharmaceutical compositions can additionally include preservatives, solubilizers, stabilizers, wetting agents, emulsifiers, sweeteners, colorants, flavorings, buffers, coating agents, or antioxidants. Compositions for oral administration can be formulated according to conventional pharmaceutical practice as described in the incorporated material in *Remington: The Science and Practice of Pharmacy* ($20^{th}$ ed, Lippincott Williams & Wilkens Publishers (2003)). For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice. The compound can also be made in microencapsulated form.

One can also administer the compounds of the invention in sustained release forms or from sustained release drug delivery systems. A description of representative sustained release materials can be found in the incorporated materials in *Remington: The Science and Practice of Pharmacy* ($20^{th}$ ed, Lippincott Williams & Wilkens Publishers (2003)).

Dosage

The selected dosage level can depend upon, for example, the condition being treated, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. It will be understood, however, that the specific dose level for any particular patient can depend upon a variety of factors including the genetic makeup, body weight, general health, diet, time and route of administration, combination with other drugs and the particular condition being treated, and its severity. For the treatment of insomnia, preferably one dose is administered prior to bedtime.

As mentioned above, in some embodiments the preferable dosage can be between about 0.001 milligrams and about 350 milligrams. In some aspects, the dosage can be about 50 milligrams to about 350 milligrams. More preferably, the dosage can be between about 75 milligrams and 300 milligrams. Also, in some aspects, the dosage can be between about 0.1 milligrams and 20 milligrams or between about 0.5 milligrams and 10 milligrams. The dosage also can be between about 1 milligram and about 6 milligrams. Preferably, the dosage can be about 0.5 milligrams, 1 milligram, about 2 milligrams, about 3 milligrams, about 4 milligrams, about 5 milligrams or about 6 milligrams. Further, the dosage can be about 7 milligrams, about 8 milligrams, about 9 milligrams, or about 10 milligrams. The lower dosage ranges are particularly desirable for sleep-related indications, while the higher dosage ranges are particularly desirable for depression and anxiety-related indications.

EXAMPLES

Example 1

Assessment of the Effect of Food on the Pharmacokinetics of Doxepin

A study assessed the effect of food on the pharmacokinetics (PK) of doxepin in healthy subjects. It was a single-center, phase 1, randomized, open-label, single dose, two-way crossover study conducted in sixteen healthy, young adult male and female subjects. Screening procedures were performed within 14 days prior to enrollment.

Following screening procedures and baseline assessments, eligible subjects were randomly assigned to one of two treatment sequences (fed-fasted or fasted-fed). Subjects received a single 6 milligram dose of doxepin in the morning under either fed or fasted conditions on 2 dosing days (Day 1 and Day 8). There were approximately 7 days between each dose. Enrolled subjects were admitted to the study center on the evening before study drug dosing (Day 0 and Day 7) and remained at the study center for approximately 5 days. All subjects were dosed under both fed and fasted conditions during the study as illustrated in FIG. 1.

Subjects being dosed under fasted conditions were required to fast overnight for at least 10 hours prior to study drug administration and for 4 hours after study drug administration. Fluids were restricted from 1 hour predose to 1 hour postdose, except for water taken at the time of dosing. Subjects being dosed under fed conditions were dosed approximately 5 minutes after eating a high-fat, high-calorie standardized breakfast (to be ingested within 25 minutes). Subjects were required to ingest the entire contents of the breakfast. All subjects were required to remain in bed for approximately 4 hours after dosing.

Contents of the high-fat, high-calorie standardized breakfast were:
  Two eggs fried in butter;
  Two slices of bacon;
  240 mL (8 fl. oz) whole milk;
  57 g (2 oz) of hash browned potatoes; and
  Two slices of toasted white bread with butter.

The total amount of protein, fat, and carbohydrate that made up this meal was approximately 33, 55, and 58 g, respectively. The total calorie content was approximately 850 kcal.

Subjects were dosed on Day 1 and Day 8. The PK profiles were evaluated on Days 1 through 5 and Days 8 through 12. Blood samples were collected at predose (0 hour) and at 0.08, 0.17, 0.25, 0.5, 0.75, 1, 1.5, 2, 3, 4, 6, 8, 12, 24, 36, 48, 60, 72, and 96 hours postdose. The samples were analyzed for doxepin and doxepin metabolite concentrations in plasma. Plasma concentrations of doxepin were measured using validated high performance liquid chromatography coupled to tandem mass spectrometry. The lower limit of quantification for doxepin was 0.05 ng/mL. The following PK parameters were estimated by noncompartmental methods using actual elapsed time from dosing:

$C_{max}$ (ng/mL) Maximum observed plasma concentration, obtained directly from the observed concentration versus time data.

$T_{max}$ (h) Time to maximum plasma concentration, obtained directly from the observed concentration versus time data.

$AUC_{0-\infty}$ (ng·h/mL) Area under the curve from time zero extrapolated to infinity, calculated by linear up/log down trapezoidal summation and extrapolated to infinity by addition of the last quantifiable concentration divided by the elimination rate constant ($AUC_{0-Tlast}+C_{last}/\lambda_z$). If the extrapolated area ($C_{last}/\lambda_z$) was greater than 30% of $AUC_{0-\infty}$ then $AUC_{0-\infty}$ was set to missing.

$AUC_{0-Tlast}$ (ng·h/mL) Area under the curve from time zero to time of last measurable concentration, calculated by linear up/log down trapezoidal summation.

$AUC_{0-24}$ (ng·h/mL) Area under the curve from time zero until 24 hours, calculated by linear up/log down trapezoidal summation. If the 24 h sample was missing or below the lower limit of quantification, $AUC_{0-Tlast}$ was to be reported as $AUC_{0-24}$.

$AUC_{0-48}$ (ng·h/mL) Area under the curve from time zero until 48 hours, calculated by linear up/log down trapezoidal summation. If the 48 h sample was missing or below the lower limit of quantification, $AUC_{0-Tlast}$ was to be reported as $AUC_{0-48}$.

$AUC_{0-72}$ (ng·h/mL) Area under the curve from time zero until 72 hours, calculated by linear up/log down trapezoidal summation. If the 72 h sample was missing or below the lower limit of quantification, $AUC_{0-Tlast}$ was to be reported as $AUC_{0-72}$.

$AUC_{0-96}$ (ng·h/mL) Area under the curve from time zero until 96 hours, calculated by linear up/log down trapezoidal summation. If the 96 h sample was missing or below the lower limit of quantification, $AUC_{0-Tlast}$ was to be reported as $AUC_{0-96}$.

$\lambda_z$ (1/h) Elimination rate constant associated with the terminal (log-linear) portion of the curve. This was estimated via linear regression of time versus log concentration. Visual assessment was used to identify the terminal linear phase of the concentration-time profile. A minimum of three data points were used for determination.

$t_{1/2}$ (h) Apparent terminal half-life, determined as ln $2/\lambda_z$.

CL/F (L/h) Apparent oral clearance, calculated as dose divided by $AUC_{0-\infty}$.

Vd/F (L) Apparent volume of distribution, calculated as $(CL/F)/\lambda_z$.

Concentration-Time Profiles

With reference to Table 1, following a single 6 milligram dose administration of doxepin in fasted state (Treatment A) and fed state (Treatment B), mean plasma concentrations of doxepin increased, reaching $C_{max}$ at 3.0 and 6.0 hours postdose, respectively. Doxepin plasma concentrations, reached mean $C_{max}$ values of 0.854 and 0.951 ng/mL in fasted and fed states, respectively. For both treatments, plasma doxepin concentrations declined thereafter and remained quantifiable up to 48 hours postdose (the lower limit of quantification was 0.05 ng/mL). Detectable plasma levels of doxepin were first observed at 30 minutes postdose in both the fed and fasted states (six and five subjects, respectively). All subjects had detectable concentrations of doxepin by 90 minutes postdose. Median $T_{max}$ was delayed by approximately 3.0 hours in the fed state (6.0 hours) as compared to the fasted state (3.0 hours). However, the range of values was similar for both treatments. Mean $t_{1/2}$ values were comparable for fed and fasted states (16.5 versus 14.4 hours, respectively).

TABLE 1

Summary Statistics [arithmetic mean (CV %)] of Plasma Doxepin Pharmacokinetic Parameters

| Parameter (unit) | Treatment [a] | |
| --- | --- | --- |
|  | Fed (N = 16) | Fasted (N = 15) |
| $C_{max}$ (ng/mL) | 0.951 (58.8) | 0.854 (63.2) |
| $T_{max}$ (h) [b] | 6.0 (2.0-6.0) | 3.0 (1.5-6.0) |
| $AUC_{0-\infty}$ (ng · h/mL) | 18.6 (70.2) | 14.1 (80.6) |
| $AUC_{0-Tlast}$ (ng · h/mL) | 16.8 (74.0) | 12.6 (85.7) |
| $t_{1/2}$ (h) | 16.5 (23.8) | 14.4 (42.2) |
| $\lambda_z$ (1/h) | 0.0445 (26.6) | 0.0623 (65.9) |

[a] 6 milligram doxepin tablet, under fed or fasted conditions.
[b] Indicates median (range) values.

Table 2 shows the estimates of clearance and volume of distribution for doxepin. Mean CL/F and Vd/F were 43% and 14% lower in the fed state compared to the fasted state, respectively. Mean CL/F values were lower in the fed (477 L/h) versus the fasted (837 L/h) states. Mean Vd/F remained almost unchanged for fed (10280 L) and fasted (11930 L) states.

TABLE 2

Summary Statistics [arithmetic mean (CV %)] of Mean Clearance and Volume of Distribution for Doxepin

| Parameter (unit) | Treatment [a] | |
|---|---|---|
| | Fed (N = 16) | Fasted (N = 15) |
| CL/F (L/h) | 477 (63.4) | 837 (114.3) |
| Vd/F (L) | 10280 (43.3) | 11930 (46.9) |

[a] 6 milligram doxepin tablet, under fed or fasted conditions.

The effect of a high-fat meal on the pharmacokinetics of the 6 milligram doxepin tablet was assessed and statistical comparisons of doxepin pharmacokinetic parameters between treatments are presented in Table 3.

The 90% confidence intervals for the ratio of population geometric least-square means between fed and fasted treatments was not completely contained within the equivalence limits of 80-125% for $C_{max}$, and were outside the equivalence limits for $AUC_{0-\infty}$ and $AUC_{0-Tlast}$, indicating that there was a food effect on exposure. Under fed conditions, $AUC_{0-\infty}$, $AUC_{0-Tlast}$, and $C_{max}$ were higher by 41%, 46%, and 15%, respectively, compared to fasted conditions.

TABLE 3

Statistical Comparison of Doxepin Pharmacokinetic Parameters Between Treatments

| Parameter (unit) | Treatment [a] | N | Geometric LS Mean | Pairwise Comparisons | | |
|---|---|---|---|---|---|---|
| | | | | Pair | Ratio (%) | 90% CI |
| $AUC_{0-\infty}$ (ng · h/mL) | Fed | 16 | 15.14 | | | |
| | Fasted | 15 | 10.72 | Fed/Fasted | 141.3 | (124.7, 160.1) |
| $AUC_{0-Tlast}$ (ng · h/mL) | Fed | 16 | 13.39 | | | |
| | Fasted | 15 | 9.194 | Fed/Fasted | 145.6 | (127.0, 166.9) |
| $C_{max}$ (ng/mL) | Fed | 16 | 0.822 | | | |
| | Fasted | 15 | 0.717 | Fed/Fasted | 114.6 | (101.8, 129.1) |

Note:
Results are based on mixed effect analysis of variance with sequence, period and treatment as fixed effects and subject within sequence as a random effect.
[a] 6 milligram doxepin tablet, under fed or fasted conditions.

CONCLUSIONS

Following a single 6 milligram dose of doxepin, a food effect was observed on the pharmacokinetics of doxepin. In the fed state, the maximum concentration ($C_{max}$) and exposure ($AUC_{0-\infty}$) of doxepin were approximately 15% and 41% higher, respectively, compared to the fasted state, and median $T_{max}$ was delayed by approximately 3.0 hours. The increase in exposure was statistically significant and represents an increase in bioavailability in the fed state (Table 4).

TABLE 4

| Parameter | Arithmetic Mean (Fed condition) | Arithmetic Mean (Fasted condition) | Effect of Food (% of fasted state)[a] |
|---|---|---|---|
| $AUC_{0-\infty}$ (ng · h/mL) | 18.6 | 14.1 | 141 |
| $C_{max}$ (ng/mL) | 0.951 | 0.854 | 115 |
| $T_{max}$ (h)[b] | 6 | 3 | 200 |

[a] Note that percentages documenting food effect on $C_{max}$ and AUC are calculated from geometric LS means rather than the arithmetic means presented in this table
[b] $T_{max}$ is presented as a median value Many modifications and variations of the embodiments described herein may be made without departing from the scope, as is apparent to those skilled in the art. The specific embodiments described herein are offered by way of example only.

We claim:
1. A method of treating insomnia, the method comprising:
   administering between about 0.5 mg and 7 mg doxepin to a patient in need thereof, wherein the doxepin is administered at least 3 hours after consuming a meal to provide faster onset of action.
2. The method of claim 1, wherein the doxepin is administered in an amount of about 3 milligrams.
3. The method of claim 1 wherein the doxepin is administered in an amount of about 6 milligrams.
4. The method of claim 1 wherein the doxepin is administered as a tablet, capsule or liquid.
5. The method of claim 1, wherein the doxepin is administered as a unit dosage form.
6. The method of claim 1, wherein the doxepin is administered as an oral dosage form.
7. The method of claim 1, wherein the doxepin helps the patient fall asleep.
8. The method of claim 1, wherein the doxepin helps the patient stay asleep.
9. The method of claim 1, wherein administration of doxepin to a group of patients after a high fat meal provides an increase in area under the curve (AUK) compared to administration of doxepin to a group of fasted patients.
10. The method of claim 9, wherein the increase in AUC is about 41%.
11. The method of claim 1, wherein administration of doxepin to a group of patients after a high fat meal provides an increase in maximum plasma concentration ($C_{max}$) compared to administration of doxepin to a group of fasted patients.
12. Claim 11, wherein the increase in $C_{max}$ is about 15%.
13. The method of claim 1, wherein the doxepin is administered within about one hour of bedtime.
14. The method of claim 1, wherein the doxepin is administered as doxepin hydrochloride.
15. A method of treating insomnia in a patient in need thereof, the method comprising:
   administering between about 0.5 mg and about 7 mg doxepin to the patient at least 3 hours after consuming a meal to provide faster onset of action, wherein administration of doxepin to a group of patients after a meal compared to administration of doxepin to a group of fasted patients provides:
   an increase in area under the curve (AUC) of doxepin;
   an increase in maximum plasma concentration (Cmax) of doxepin; or
   a delay in median time to reach maximum plasma concentration ($T_{max}$) of doxepin.

16. The method of claim 15, wherein the increase in AUC is about 41%.

17. The method of claim 15, wherein the increase in maximum plasma concentration ($C_{max}$) is about 15%.

18. The method of claim 15, wherein the a delay in median time to reach maximum plasma concentration ($T_{max}$) is about 3 hours.

19. The method of claim 15, wherein administration of doxepin to a group of fasted patients provides:
- an increase in area under the curve (AUC) is about 41%;
- an increase in maximum plasma concentration ($C_{max}$) is about 15%; or
- a delay in median time to reach maximum plasma concentration ($T_{max}$) is about 3 hours.

* * * * *

UNITED STATES PATENT AND TRADEMARK OFFICE
CERTIFICATE OF CORRECTION

PATENT NO. : 11,110,074 B2
APPLICATION NO. : 16/876492
DATED : September 7, 2021
INVENTOR(S) : Cara Baron Casseday et al.

Page 1 of 1

It is certified that error appears in the above-identified patent and that said Letters Patent is hereby corrected as shown below:

In the Claims

Column 16, Line 41, Claim 9 replace "(AUK)" after "the curve" and before "compared to" with "(AUC)".

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*